United States Patent [19]

Relyea et al.

[11] 4,174,405
[45] Nov. 13, 1979

[54] THIOPHENES USEFUL IN CONTROL OF ACARIDS

[75] Inventors: Douglas I. Relyea, Bethany; Winchester L. Hubbard, Woodbridge; Robert E. Grahame, Jr., Cheshire, all of Conn.

[73] Assignee: Uniroyal, Inc., New York, N.Y.

[21] Appl. No.: 840,687

[22] Filed: Oct. 11, 1977

Related U.S. Application Data

[63] Continuation-in-part of Ser. No. 691,660, Jun. 1, 1976, abandoned, which is a continuation-in-part of Ser. No. 445,378, Feb. 25, 1974, abandoned.

[51] Int. Cl.² .................... A01N 9/00; C07D 333/16; C07D 333/12
[52] U.S. Cl. .................... 424/275; 549/60; 549/65; 549/66; 549/62; 549/78; 549/80; 549/74
[58] Field of Search .................... 424/275; 260/329 R, 260/332.5, 332.3 R

[56] References Cited

U.S. PATENT DOCUMENTS 3,644,399  2/1972  Brown et al. .................... 424/275

OTHER PUBLICATIONS

Hartough, "Thiophene & Dir", (1952), pp. 468–478.

*Primary Examiner*—A. Siegel
*Attorney, Agent, or Firm*—James J. Long

[57] ABSTRACT

Substituted thiophenes of the following formula, some of which are new compounds, are useful in controlling certain pests, particularly mites:

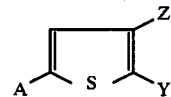

wherein A, Y and Z are various substituents such as phenyl and substituted phenyl.

56 Claims, No Drawings

THIOPHENES USEFUL IN CONTROL OF ACARIDS

This application is a continuation-in-part of our application Ser. No. 691,660, filed June 1, 1976 (now abandoned), which is in turn a continuation-in-part of our application Ser. No. 445,378, filed Feb. 25, 1974, now abandoned; the disclosures of the said applications are hereby incorporated herein by reference. Our related copending application Ser. No. 678,789, filed Apr. 21, 1976 (now abandoned) is a division of said abandoned application Ser. No. 445,378.

This invention relates to a method of controlling acarids, especially mites, using certain substituted thiophenes, as well as compositions and new chemical compounds useful in such method.

Plant-feeding mites produce enormous losses to agricultural crops such as alfalfa, apples, corn, cotton, grapes, oranges, grapefruit, potatoes, sorghum, peanuts and many others.

In addition, various species have become so specialized in structure and habit that they must subsist on the bodies of man and animals. Few domesticated or wild animals are immune to their attack.

Other species such as itch and mange mites cause serious skin diseases in animals such as dogs, cats, rabbits, horses, cattle and pigs.

Ticks and some species of mites suck the blood of man and animals. Besides the irritation involved, a multitude of animal diseases may be transmitted by this method of food procurement. Dread diseases such as Rocky Mountain spotted fever, relapsing fever and tularemia are transmitted by the bites of ticks.

During the last thirty years, numerous chemicals have been utilized in protecting both man and man's food and fiber against injury from mites and ticks. There is a continuing need for novel, effective and safe chemicals to accomplish this task.

In accordance with the invention it has now been found that certain substituted thiophenes are useful in the control of acarids. The substituted thiophenes employed in the control of the said pests in the method of the invention are those of the formula

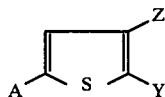

wherein A, Y and Z may be the same or different and are as follows:

A is phenyl, naphthyl, or substituted phenyl carrying one or more substituents, said substituents being fluorine, chlorine, bromine, nitro, alkyl having 1 to 5 carbon atoms, cycloalkyl having 5 or 6 carbon atoms, phenyl, alkoxy having 1 to 3 carbon atoms, alkylthio having 1 to 3 carbon atoms, alkylenedioxy having 1 or 2 carbon atoms or halomethyl having 1 to 3 halogen atoms selected from fluorine, chlorine and bromine;

Y has the meanings of A and additionally is hydrogen, fluorine, chlorine, bromine, phenylthio, phenylsulfono, or phenylthio substituted with one or more of the substituents fluorine, chlorine, bromine, nitro, alkyl having 1 to 5 carbon atoms, cycloalkyl having 5 or 6 carbon atoms, alkoxy having 1 to 3 carbon atoms or halomethyl having 1 to 3 halogen atoms selected from fluorine, chlorine and bromine; and Z is hydrogen, phenyl or phenyl having one or more substituents, said substituents being fluorine, chlorine, bromine, nitro, alkyl having 1 to 5 carbon atoms, alkoxy having 1 to 3 carbon atoms and halomethyl having 1 to 3 halogen atoms selected from fluorine, chlorine and bromine.

In another aspect of the method of the invention there is employed a substituted thiophene of the foregoing formula wherein:

A is phenyl, phenyl substituted with fluorine, chlorine, alkyl having 1 to 4 carbon atoms, phenyl, methoxy, methylthio, trifluoromethyl or nitro; Y is hydrogen, bromine, phenyl, phenylthio or substituted phenyl or phenylthio having substituents selected from chlorine and methoxy; and Z is hydrogen, phenyl or phenyl substituted with fluorine, chlorine or methoxy.

Certain compounds within the above formula are new, namely those wherein:

A is phenyl, naphthyl or phenyl substituted with one or more radicals selected from fluorine, chlorine, bromine, nitro, alkyl having 1 to 5 carbon atoms, cycloalkyl having 5 to 6 carbon atoms, phenyl, alkoxy having 1 to 3 carbon atoms, alkylenedioxy having 1 to 2 carbon atoms, alkylthio having 1 to 3 carbon atoms, and halomethyl carrying 1 to 3 atoms selected from fluorine, bromine and chlorine, provided that when Y and Z are hydrogen A is not phenyl substituted with halogen, nitro, alkyl, and alkoxy, and when Y is hydrogen, halogen and phenyl and Z is hydrogen or phenyl A is not phenyl, alkaryl or naphthyl;

Y is hydrogen, fluorine, chlorine, bromine, phenyl, naphthyl, phenylthio, substituted phenyl or substituted phenylthio having one or more substituents, said substituents being fluorine, chlorine, bromine, nitro, alkyl having 1 to 5 carbon atoms, cycloalkyl having 5 or 6 carbon atoms, phenyl, alkoxy having 1 to 3 carbon atoms, alkylthio having 1 to 3 carbon atoms, alkylenedioxy having 1 or 2 carbon atoms, or halomethyl having 1 to 3 halogen atoms wherein the halogen is fluorine, chlorine or bromine; and Z is hydrogen, phenyl or substituted phenyl having one or more substituents, said substituents being fluorine, chlorine, bromine, nitro, alkyl having 1 to 4 carbon atoms, alkoxy having 1 to 3 carbon atoms, or halomethyl having 1 to 3 halogen atoms wherein the halogen is fluorine, chlorine or bromine.

Of the foregoing new compounds, a preferred class is represented by those wherein A is phenyl or phenyl substituted with fluorine, chlorine, bromine, alkyl having 1 to 5 carbon atoms, cyclopentyl, phenyl, trifluoromethyl, methoxy or methylthio; Y is hydrogen, phenyl, phenylthio, substituted phenyl or phenylthio groups substituted with chlorine, nitro or methoxy, and Z is hydrogen, phenyl or phenyl substituted with fluorine, chlorine or methoxy.

One aspect of the invention involves controlling acarid pests by applying an acricidal amount of a substituted thiophene of the formula

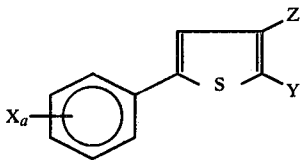

where X is alkyl having 1 to 3 carbon atoms, halogen, nitro, haloalkyl having 1 to 3 carbon atoms, alkoxy having 1 to 3 carbon atoms, alkylthio having 1 to 3 carbon atoms or phenyl; a is 0, 1 or 2; Y is hydrogen, halogen, phenyl, phenylthio, nitrophenylthio, chlorophenylthio, or phenylsulfono; and Z is hydrogen or phenyl; in this aspect of the invention certain new chemicals are involved, namely, those wherein a, X, Y and Z have one of the following sets of values:

| a | X | Y | Z |
|---|---|---|---|
| 0 | — | $C_6H_5S$ | H |
| 0 | — | $C_6H_5SO_2$ | H |
| 0 | — | $C_6H_5S$ | $C_6H_5$ |
| 0 | — | $p\text{-}ClC_6H_5S$ | H |
| 1 | $p\text{-}SCH_3$ | H | H |
| 1 | $o\text{-}C_6H_5$ | H | H |
| 1 | $p\text{-}CH_3$ | $C_6H_5S$ | H |
| 1 | $p\text{-}(CH_3)_2CH$ | $C_6H_5S$ | H |
| 1 | $m\text{-}Cl$ | $C_6H_5S$ | H |
| 1 | $m\text{-}CF_3$ | $C_6H_5S$ | H |
| 1 | $p\text{-}Br$ | $m\text{-}O_2NC_6H_5S$ | H |
| 1 | $p\text{-}OCH_3$ | $C_6H_5S$ | H |
| 2 | $3,4\text{-}(CH_3)_2$ | H | H |
| 2 | $3,4\text{-}(CH_3)_2$ | $C_6H_5S$ | H |

Compounds useful in the invention may be prepared by various methods. Thus, 2-substituted thiophenes may be prepared by an anhydrous version (C. M. Camaggi, R. Leardini, M. Tiecco and A. Tundo, J. Chem. Soc., B 1683 [1970]) of the Gomberg-Bachmann free radical arylation reaction (M. Gomberg and W. E. Bachmann, J.A. Chem. Soc., 46, 2339 [1924]). n-Butyl nitrite may be used as the diazotizing reagent and a 20 to 25-fold excess of thiophene may serve both as solvent and diluent to reduce the extent of disubstitution. Free radical arylation of thiophenes proceeds about 95% in the alpha-position. The distilled or recrystallized arylthiophenes are generally greater than 98% pure. Reaction times are 3–7 days at room temperature and yields are mainly in the upper half of the 20–50% range.

Similarly, phenylthio-substituted arylthiophenes may be prepared by a Friedel-Crafts substitution using benzenesulfenyl chloride as the electrophilic reagent (T. Fujisawa, T. Kobori, N. Ohtsuka and G. Tsuchihashi, Tetr. Letters, No. 49, 5071 [1968]).

As representative chemicals useful in the invention there may be mentioned by way of non-limiting example such compounds as:
2-p-chlorophenyl-3,5-diphenylthiophene
2,3-di(p-tolyl)-5-phenylthiophene
2,3,5-tri(p-tolyl)thiophene
2,3-di-(p-chlorophenyl)-5-phenylthiophene
2,3-di(p-chlorophenyl)-5-p-tolylthiophene
2,3-diphenyl-5-p-ethylphenylthiophene
2,3,5-tri(p-anisyl)thiophene
2,3-diphenyl-5-(3,4-dimethylphenyl)thiophene
2,3-di(p-bromophenyl)-5-p-tolylthiophene
2,3-diphenyl-5-p-ethoxyphenylthiophene
2,5-diphenyl-3-m-tolylthiophene
2,5-diphenyl-3-p-anisylthiophene
2,5-diphenyl-3-(3,4-dimethylphenyl)thiophene
2,3-(3,4-dimethoxyphenyl)-5-phenylthiophene
2,5-diphenyl-3-p-bromophenylthiophene
2,5-diphenyl-3-p-fluorophenylthiophene
2,5-diphenyl-3-p-nitrophenylthiophene
2,3-diphenyl-5-m-nitrophenylthiophene
2,5-diphenyl-3-m-trifluoromethylphenylthiophene
2,3-diphenyl-5-(3,4,5-trimethoxyphenyl)thiophene
2,3-diphenyl-5-m-trifluoromethylphenylthiophene
2-p-tolyl-3,5-di(p-bromophenyl)thiophene
2,5-diphenyl-3-p-ethoxyphenylthiophene
2,3-diphenyl-5-m-methoxyphenylthiophene
2,3-bis(p-tolyl)-5-phenylthiophene
2,5-diphenyl-3-(3,4-dimethylphenyl)thiophene
2,5-diphenyl-3-p-ethoxyphenylthiophene
2,3-bis(2-chlorophenyl)-5-phenylthiophene
2,5-diphenyl-3-o-tolylthiophene
2-m-nitrophenyl-3-p-methoxyphenyl-5-p-tolylthiophene
2,3-bis(p-methoxyphenyl)-5-m-tolythiophene
2,3-diphenyl-5-(3,4-dimethoxyphenyl)thiophene
2,3-diphenyl-5-(2,3,4-trichlorophenyl)thiophene
2,3-diphenyl-5-(2,4-dimethoxyphenyl)thiophene
2-(3-nitrophenyl)-5-phenylthiophene
2-(4-nitrophenyl)-5-phenylthiophene
2-(3-chlorophenylthio)-5-phenylthiophene
2-(4-chlorophenylthio)-5-phenylthiophene
2-(4-anisyl)-5-phenylthiophene
2-(4-nitrophenylthio)-5-phenylthiophene
2-(1-naphthyl)-5-phenylthiophene
2-(2-naphthyl)-5-phenylthiophene
2-(1-anthryl)-5-phenylthiophene
2-(9-phenanthryl)-5-phenylthiophene
2-(3-nitrophenyl)-5-(p-tolyl)thiophene
2-(p-bromophenyl)-3,5-diphenylthiophene
2-(m-nitrophenyl)-5-(phenylthio)thiophene
2-(p-ethoxyphenyl)-5-(3-chlorophenylthio)thiophene
2-(4-anisyl)-5-(t-butylphenylthio)thiophene
3,5-diphenyl-2-(o-propylphenyl)thiophene
2-(1-naphthyl)-5-(m-nitrophenyl)thiophene
5-(p-chlorophenyl)-2-(2-naphthyl)-3-phenylthiophene
2-(1-anthryl)-5-(p-trichloromethylphenyl)thiophene
2-(4-chlorophenylthio)-5-(p-tolyl)thiophene
2-(p-biphenylyl)-5-(p-tolyl)thiophene
2-(3-nitrophenyl)-5-phenylthio-thiophene
2-(4-nitrophenyl)-5-phenylthiothiophene
2-(3-methylthiophenyl)-5-phenylthiothiophene
2-(4-methylthiophenyl)-5-phenylthiophene
2-(2-anisyl)-5-phenylthiothiophene
2-(3-chlorophenyl)-5-phenylthiothiophene
2-(1-napthyl)-5-phenylthiothiophene
2-(2-naphthyl)-5-phenylthiothiophene
2-(1-anthryl)-5-phenylthiothiophene
2-(9-phenanthryl)-5-phenylthiothiophene
2-(3-nitrophenyl)-5-(p-tolythio)thiophene
2-(4-nitrophenyl)-5-(p-chlorophenylthio)thiophene
2-(3-nitrophenylthio)-3,5-diphenylthiophene
3,5-diphenyl-2-(p-tolylthio)thiophene
2-(4-anisyl)-3,5-diphenylthiophene
2-(2-naphthyl)-4-phenyl-5-phenylthiothiophene
2-(4-anisyl)-5-phenylsulfonylthiophene
2-phenylsulfonyl-5-(3,4-xylyl)thiophene
2-(4-chlorophenyl)-5-phenylsulfonylthiophene
2-(p-methoxyphenylsulfonyl)-5-phenylthiophene
2-(p-chlorophenylsulfonyl)-3,5-diphenylthiophene
2-phenyl-5-(p-tolylsulfonyl)thiophene
2-(1-naphthyl)-4-phenylthiophene 2-(2-naphthyl)-4-phenylthiophene
2-(1-anthryl)-4-phenylthiophene
2-(9-phenanthryl)-4-phenylthiophene
2-chloro-3-(4-nitrophenyl)-5-(p-tolyl)thiophene
2-(4-nitrophenylthio)-3,5-diphenylthiophene
2-bromo-3,5-bis(p-propyloxyphenyl)thiophene
2-(p-tert-butylphenylthio)-5-(p-chlorophenyl)thiophene
2-(4-nitrophenylthio)-5-(3,5-xylyl)thiophene
2-(4-chlorophenylthio)-5-(3,4-methylenedioxy phenyl)-thiophene
5-(1-naphthyl)-2-(p-trifluoromethylphenyl)thiophene
2-(p-ethylthiophenyl)-5-(4-nitrophenylthio)thiophene
2-(p-biphenylyl)-5-(4-chlorophenylthio)thiophene
2-(2-nitrophenylthio)-3,5-diphenylthiophene
2-(p-trifluoromethylphenyl)-3,5-diphenylthiophene
2-(p-chlorophenylthio)-3,5-diphenylthiophene
2-(m-chlorophenylthio)-3,5-diphenylthiophene
2-(p-methoxyphenylthio)-3,5-diphenylthiophene
2-(m-trifluoromethylphenyl)-3,5-diphenylthiophene
2,4-diphenyl-5-(1-naphthyl)thiophene
2,4-diphenyl-5-(2-naphthyl)thiophene
5-(1-anthryl)-2,4-diphenylthiophene
2,4-diphenyl-5-(9-phenanthryl)thiophene
3,5-bis(p-chlorophenyl)-2-phenylthiothiophene
2-phenylthio-3,5-bis-(p-tolyl)thiophene
3,5-bis(p-bromophenyl)-2-phenylthiothiophene
3,5-di-p-anisyl-2-phenylthiothiophene
3,5-di-p-anisyl-2-(p-chlorophenylthio)thiophene
2-(p-chlorophenylthio)-3,5-diphenylthiophene
2-(m-chlorophenylthio)-3,5-diphenylthiophene
5-(3,4-dimethoxyphenyl)-2,3-diphenylthiophene
3,5-diphenyl-2-(p-cyclohexylphenylthio)thiophene
3,5-diphenyl-2-(p-phenylphenylthio)thiophene
2,5-diphenyl-3-(p-cyclopentylphenyl)thiophene
2,5-diphenyl-3-(p-phenylphenyl)thiophene
3,5-diphenyl-2-(p-fluorophenyl)thiophene
2-p-chlorophenyl-3,5-diphenylthiophene
2,3,5-tri(p-anisyl)thiophene
2,3-diphenyl-5-(3,4-dimethylphenyl)thiophene
2,3-di(p-bromophenyl)-5-p-tolylthiophene
2,3-diphenyl-5-m-nitrophenylthiophene
2,3-diphenyl-5-(3,4,5-trimethoxyphenyl)thiophene
2,3-diphenyl-5-m-trifluoromethylphenylthiophene
2-p-tolyl-3,5-di(p-bromophenyl)thiophene
2-fluoro-3,5-diphenylthiophene
2-chloro-3,5-diphenylthiophene
2,3-bis(p-isopropylphenyl)-5-phenylthiophene Also of interest are compounds wherein Y and/or Z of the above formula represent such substituents as polycyclic aryl groups having more than 10 carbon atoms, or phenylsulfonyl (unsubstituted or substituted with such moieties as halogen, alkyl, alkoxy, nitro, and the like), as well as compounds wherein Z has the meanings halogen such as fluorine and chlorine, phenyl carrying substituents such as cycloalkyl, alkylenedioxy, or wherein Z may be naphthyl, phenylthio and substituted phenylthio.

The invention is practiced by applying to a locus, subject to attack by acarids, an effective amount, viz., an acaricidal amount, of a chemical of the kind described. Frequently the locus is either plant life, for example such crops as alfalfa, apples, corn, cotton, grapes, oranges, grapefruit, potatoes, sorghum, peanuts, etc., or animal life, and man. The chemicals may be applied alone or with a carrier, which may enhance the effectiveness of the active agent or facilitate handling, to loci to be protected against mites or the like, for example as dusts when admixed with or absorbed on powdered solid carriers, such as the various mineral silicates, e.g., mica, talc, pyrophillite and clays, or as liquids or sprays when in a liquid carrier, as in solution in a suitable solvent, such as acetone, benzene or kerosene, or dispersed in a suitable nonsolvent medium, for example, water. In protecting plants (the term including plant parts) which are subject to attack by these pests, the chemicals of the present invention are preferably applied as aqueous emulsions containing a surface-active dispersing agent, which may be an anionic, nonionic or cationic surface-active agent. Such surface-active agents are well known and reference is made to U.S. Pat. No. 2,547,724 columns 3 and 4 for detailed examples of the same. The chemicals of the invention may be mixed with such surface-active dispersing agents, with or without an organic solvent, as acaricidal concentrates for subsequent addition of water to make aqueous suspensions of the chemicals of the desired concentration. The chemicals of the invention may be admixed with powdered solid carriers, such as mineral silicates, together with a surface-active dispersing agent so that a wettable powder may be obtained, which may be applied directly to loci to be protected against mites or the like, or which may be shaken up with water to form a suspension of the chemical (and powdered solid carrier) in water for application in that form. The chemicals of the present invention may be applied to loci to be protected against mites or insects by the aerosol method. Solutions for the aerosol treatment may be prepared by dissolving the chemical directly in the aerosol carrier which is liquid under pressure but which is a gas at ordinary temperature (e.g., 20° C.) and atmospheric pressure, or the aerosol solution may be prepared by first dissolving the chemical in a less volatile solvent and then admixing such solution with the highly volatile liquid aerosol carrier. The chemicals may be used admixed with carriers that are active of themselves, for example, insecticides, fungicides, bactericides, and other acaricides.

Practical formulations ordinarily contain from 1 to 95% active ingredient. Spray dilutions may range from a few parts per million to undiluted concentrate applied by ultra low volume techniques. The concentration of chemical per acre would vary depending upon many factors, but normally range from from 0.1 to 10 pounds.

In one aspect, the invention is directed to new compositions useful in the control of acarids comprising the described substituted thiophene chemical, in acaricidally effective amount, in combination with a carrier therefor.

The following examples will serve to illustrate the practice of the invention in more detial.

EXAMPLE 1

2-(p-Methylthiophenyl)thiophene

In a 4-l Erlenmeyer flask were placed 69.5 g (0.400 mole) 4-(methylthio)aniline hydrochloride, 500 ml of thiophene and 40.5 g of triethylamine. The mixture was stirred 10 minutes at room temperature. Thiophene (2000 ml, total 31.8 moles) and 65 ml (0.58 mole) of n-butyl nitrite were added. The mixture was then stirred at room temperature (23° C.) for 14 days.

The reaction mixture was divided into two equal portions, each of which was washed with three 500 ml portions of water. The organic residues were then concentrated by evaporation of unreacted thiophene. The concentrated residue was then distilled at reduced pressure to give 19 g (23%) of 2-(p-methylthiophenyl)thiophene, b.p. 135°–146° C. (0.1 mm), a yellow solid melting at 108°–110° C.

Anal. Calc'd for $C_{11}H_{10}S_2$: C, 64.03; H, 4.89; Found: C, 64.44; H, 4.82.

EXAMPLE 2

2-(o-Biphenylyl)thiophene

In a 4-l Erlenmeyer flask were placed 100 g (0.600 mole) of Pfalz and Bauer o-aminobiphenyl, m.p. 49°–51° C., 3000 ml (38.2 moles) of thiophene and 90 ml (0.80 mole) of n-butyl nitrite. The mixture was thoroughly stirred and then allowed to stand at room temperature for eight days. Unreacted thiophene was removed by distillation. The residue was distilled at reduced pressure to give 49.4 g (34.8%) of 2-(o-biphenylyl)thiophene b.p. 138°–155° C. (0.1 mm), $N_D^{20}$ 1.6465.

EXAMPLE 3

2-Phenyl-5-(phenylthio)thiophene

In a 500 ml flask were placed 36.9 g (0.23 mole) of 2-phenylthiophene, 200 ml of reagent carbon tetrachloride, 36.9 g (0.26 mole) of benzenesulfenyl chloride and 0.2 g of iron powder. The reaction mixture was allowed to stand four days at room temperature. Distillation of the carbon tetrachloride gave a crystalline residue which was recrystallized first from ethanol-ethyl acetate (9:1) and then from ethyl acetate-pentane (1:9) to give 10.6 g (17%) of 2-phenyl-5-(phenylthio)thiophene, m.p. 72.5°–74.5° C.

Anal. Calc'd for $C_{16}H_{12}S_2$: C, 71.60; H, 4.51; S, 23.90. Found: C, 70.98; H, 4.47; S, 23.61.

The infrared spectrum showed the presence of both the phenyl and the phenylthio group by the absorption maxima at 761 cm$^{-1}$ and 744 cm$^{-1}$.

EXAMPLE 4

2-Phenyl-5-(phenylsulfonyl)thiophene

A solution of 2.68 g (10 mmoles) of 2-phenyl-5-(phenylthio)thiophene in 30 ml of acetic acid was treated with 4 ml (40 mmoles) of 30% hydrogen peroxide and allowed to stand 16 hours. Filtration separated a first crop of 1.70 g. Chilling the filtrate to 4° C. and refiltration gave a second crop of 0.33 g, m.p. 115°–116.5° C. The total yield of 2.03 g is 68% of the theoretical for 2-phenyl-5-(phenylsulfonyl)thiophene.

Anal. Calc'd for $C_{16}H_{12}O_2S_2$: C, 63.97; H, 4.03; S, 21.36. Found: C, 64.02; H, 3.93; S, 2052.

The presence of a sulfone group, rather than two sulfoxide groups, in the product is demonstrated by the two strong infrared absorption maxima at 1320 cm$^{-1}$ (S-O symmetrical vibration) and 1150 cm$^{-1}$ (S-O asymmetrical vibration) characteristic of the sulfone group. The fact that oxidation occurred at the phenylthio sulfur, in preference to the thiophene ring sulfur, is shown by the proton magnetic resonance spectrum. This spectrum shows two ortho protons of a phenylsulfonyl group at 7.97–8.17δ and ten other protons farther upfield (7.19–7.67δ).

EXAMPLE 5

2-Phenylthio-5-p-tolylthiophene

Into 500 ml of reagent carbon tetrachloride were added 61 g (0.35 mole) of 2-p-tolylthiophene, 41 ml (51 g, 0.35 mole) of benzenesulfenyl chloride and 0.05 g of powdered iron. The reaction mixture was allowed to stand four days at room temperature after which the carbon tetrachloride was distilled off and the 45-gram residue washed with a mixture of 80 ml of ether and 250 ml of petroleum ether. Recrystallization of the washed solid from 300 ml of ethanol gave 28 g (29%) of 2-phenylthio-5-p-tolylthiophene, m.p. 85°–86° C.

Anal. Calc'd for $C_{17}H_{14}S_2$: C, 72.30; H, 5.00; S, 22.71. Found: C, 72.53; H, 4.97; S, 22.02.

The structure is confirmed by the proton magnetic resonance spectrum which shows a ratio of 3 aliphatic protons (as methyl groups, 2.34δ) to 11 aromatic protons (7.11–7.49δ).

EXAMPLE 6

2-(p-Isopropylphenyl)-5-(phenylthio)thiophene

Into 150 ml of reagent carbon tetrachloride were added 29 g (0.143 mole) 2-(p-isopropylphenyl)thiophene, 17 ml (21 g, 0.145 mole) of benzenesulfenyl chloride and 0.05 g of iron powder. At the end of four days a vapor phase chromatogram of the reaction mixture showed the presence of diphenyl disulfide, unreacted 2-(p-isopropylphenyl)thiophene and the desired product. An additional 4 ml (5 g, 0.035 mole) of benzenesulfenyl chloride and 0.05 g of iron powder was added and the mixture allowed to stand another four days at room temperature. Evaporation of the carbon tetrachloride gave a residue which was twice recrystallized from 250-ml portions of petroleum ether. There was obtained 16 g (36%) of 2-(p-isopropylphenyl)-5-(phenylthio)thiophene, m.p. 61°–63° C.

Anal. Calc'd for $C_{19}H_{18}S_2$: C, 73.50; H, 5.84; S, 20.65. Found: C, 73.22; H, 5.75; S, 20.59.

EXAMPLE 7

2-(m-Chlorophenyl)-5-(phenylthio)thiophene

A mixture of 89 g (0.46 mole) of 2-(m-chlorophenyl)thiophene, 400 ml of reagent carbon tetrachloride, 54 ml (67 g, 0.46 mole) of benzenesulfenyl chloride and 0.05 g of iron powder was allowed to stand for four days at room temperature. A further 12 ml (15 g, 0.10 mole) of benzenesulfenyl chloride and 0.05 g of iron powder were added. After four days the carbon tetrachloride was removed by distillation. The residue was distilled at reduced pressure to give 30 g (22%) of 2-(m-chlorophenyl)-5-(phenylthio)thiophene, b.p. 200°–205° C. (0.15 mm).

Anal. Calc'd for $C_{16}H_{11}ClS_2$: C, 63.46; H, 3.66; Cl, 11.71; S, 21.18. Found: C, 63.20; H, 3.65; Cl, 12.04; S, 21.37.

EXAMPLE 8

2-Phenylthio-5-(m-trifluoromethylphenyl)thiophene

A mixture of 29.7 g (0.13 mole) of 2-(m-trifluoromethylphenyl)thiophene, 200 ml of reagent carbon tetrachloride, 15.5 ml (18.8 g 0.13 mole) of benzene sulfenyl chloride and 0.05 g of iron powder was allowed to stand 4 days at room temperature. The reaction mixture was found by vapor phase chromatography to contain approximately equal amounts of 2-(m-trifluoromethylphenyl)thiophene, diphenyl disulfide and the desired disubstituted thiophene. An additional 12.7 ml (0.11 mole) of benzenesulfenyl chloride and 0.05 g of iron powder were added. The mixture was stirred 2 hours at room temperature and then 1 hour at reflux. The carbon tetrachloride solvent was removed by distillation. The residue was distilled at reduced pressure to give 17 g (39%) of 2-phenylthio-5-(m-trifluoromethylphenyl)thiophene b.p. 172°–210° C. (0.04 mm), $n_D^{21}$ = 1.6329–1.6330.

Anal. Calc'd for $C_{17}H_{11}F_3S_2$: C, 60.70; H, 3.30; S, 19.06. Found: C, 59.39; H, 3.35; S, 18.73.

The low value found for carbon probably arises from the difficulty in quantitatively converting the carbon of the trifluoromethyl group to carbon dioxide under the combustion analysis conditions.

EXAMPLE 9

2-(3,4-Xylyl)thiophene

A solution of 182 g (1.50 moles) of 3,4-dimethylaniline, m.p. 49°–51° C. in 3000 ml (38 moles) of thiophene was treated with 226 ml (2.00 moles) of n-butyl nitrite. The solution was allowed to stand at room temperature for one week. Unreacted thiophene was removed by distillation with a steam bath. The residue was distilled at reduced pressure to give 75 g (27%) of 2-(3,4-xylyl)thiophene, b.p. 107°–122° (0.08 mm). Vapor phase chromatography showed the presence of about 2% of the xylidine starting material, removed by washing first with two 100-ml portions of 10% hydrochloric acid followed by two 150-ml portions of distilled water.

Anal. Calc'd for $C_{12}H_{12}S$: C, 76.55; H, 6.43; S, 17.03. Found: C, 76.11; H, 6.51; S, 15.26.

EXAMPLE 10

2-Phenylthio-5-(3,4-xylyl)thiophene

A mixture of 37 g (0.197 mole) of 2-(3,4-xylyl)thiophene, 200 ml of reagent carbon tetrachloride, 29 ml (36 g, 0.259 mole) of benzenesulfenyl chloride and 0.05 g of iron powder was allowed to stand two days at room temperature. A vapor phase chromatogram of the mixture showed that all the 2-(3,4-xylyl)thiophene had been consumed. The carbon tetrachloride was removed by distillation and the residue recrystallized from ethanol to give a first crop of 17 g (29%) of 2-phenylthio-5-(3,4-xylyl)thiophene, m.p. 77°–78° C.

Anal. Calc'd for C H S: C, 72.93; H, 5.44; S, 21.63. Found: C, 73.17; H, 5.33; S, 22.18.

The proton magnetic resonance spectrum showed a ratio of six methyl protons (2.26δ) to ten aromatic protons (7.06–7.33δ)

EXAMPLE 11

3,5-Diphenyl-2-(phenylthio)thiophene

A solution of 17.7 g (75 mmoles) of 2,4-diphenylthiohene in 300 ml of carbon tetrachloride was treated with 8.7 ml 10.8 g (75 mmoles) of benzenesulfenyl chloride and allowed to stand for one week. The solvent was removed by evaporation. The residue was washed with ether to obtain 14 g of crude product which was recrystallized from ethyl acetate. There was obtained 10.5 g (41%) of 3,5-diphenyl-2-(phenylthio)thiophene, m.p. 96°–97° C.

Anal. Calc'd for $C_{22}H_{16}S_2$: C, 76.70; H, 4.68; S, 18.61. Found: C, 76.70; H, 4.56; S, 18.27.

EXAMPLE 12

2-(p-Bromophenyl)-5-(m-nitrophenylthio)thiophene

To a solution of 21.2 g (0.112 mole) of m-nitrobenzenesulfenyl chloride in 160 ml of carbon tetrachloride were added 24.5 g (0.103 mole) of 2-(p-bromophenyl)thiophene and 0.1 g of iron powder. The reaction mixture was allowed to stand one week at room temperature. Evaporation of the solvent and recrystallization of the residue from 140 ml of ethyl acetate gave 17.6 g (44%) of 2-(p-bromophenyl)-5-(m-nitrophenylthio)thiophene, m.p. 120°–122° C.

Anal. Calc'd for $C_{16}H_{10}BrNo_2S_2$: C, 48.99; H, 2.57; Br, 20.37; N, 3.57; S, 16.35. Found: C, 48.87; H, 2.54; Br, 20.50; N, 3.95; S, 16.04.

EXAMPLE 13

2-p-Anisyl-5-(phenylthio)thiophene

A solution of 34 g (0.179 mole) of 2-p-anisylthiophene in 500 ml of carbon tetrachloride was treated with 23 ml (28.5 g, 0.197 mole) of benzenesulfenyl chloride and 0.1 g of iron powder. The mixture was allowed to stand at room temperature for eight days. The mixture was filtered to remove a small amount of solid. The filtrate was evaporated to give 67 g of crude solid product. Recrystallization from 220 ml of ethyl acetate gave 15.4 g (29%) of 2-p-anisyl-5-(phenylthio)thiophene, m.p. 92°–93° C.

Anal. Calc'd for $C_{17}H_{14}OS_2$: C, 68.42; H, 4.73; S, 21.49. Found: C, 69.09; H, 4.73; S, 20.93.

EXAMPLE 14

2-(p-Chlorophenylthio)-5-phenylthiophene

A solution of 40 g (0.250 mole) of 2-phenylthiophene in 200 ml of carbon tetrachloride was treated at room temperature with 45 g (0.252 mole) of p-chlorobenzenesulfenyl chloride. Iron powder (0.1 g) was added and the reaction mixture was allowed to stand for seven days at room temperature. Filtration removed a small amount of insoluble material. Evaporation of the filtrate gave a residue of 79.8 g of crude product, m.p. 85°–87° C. Recrystallization of the residue from 400 ml of absolute ethanol gave 40 g (53%) of 2-(p-chlorophenylthio)-5-phenylthiophene, m.p. 101°–103° C.

Anal. Calc'd for $C_{16}H_{11}ClS_2$: C, 63.46; H, 3.66; Cl, 11.71; S, 21.18. Found: C, 63.65; H, 3.79; Cl, 11.55; S, 20.52.

EXAMPLE 15

Mite Contact Test

Cotton, *Gossypium hirsutum* L.—variety Stoneville—213, in the second primary leaf stage, grown in twelve-ounce cups under greenhouse conditions at 70°–75° F., was used in this test. One plant (two primary leaves) in one pot was used for each replicate; two replicates were used for each chemical tested. A one-inch diameter circle of tree tanglefoot, a sticky, non-toxic preparation, was used to confine the mites to the upper leaf surfaces. Approximately twenty-five adult two-spotted spider mites (*Tetranychus urticae*) were transferred to each test plant 24 hours prior to treatment.

Test compounds were prepared for spraying at 1000 ppm (parts per million) concentration by dissolving them in a small amount of acetone and adding a suitable wetting agent. Typically, 0.6 grams of chemical were dissolved (or suspended) in 10 ml of acetone, two drops of Triton-X100 (trademark; octylphenoxy polyethoxy ethanol with 9–10 mole percent of polyethylene oxide) wetting agent were added and this was suspended in 100 ml of water to make a 6000 ppm suspension. An aliquot was then further diluted with distilled water to 1000 ppm concentration of chemical.

The infested plants were sprayed with the dispersions using a small spray atomizer to thoroughly drench the foliage. The plants were returned to the greenhouse where they were held for six days. After this period the plants were examined for adult live mites remaining on the leaves. On an estimation basis and in comparison with the number of living mites on the check plants, the percent control was determined.

Data for the mite contact test are shown in Table I, wherein chemicals 1 to 13 correspond to the compounds prepared in Examples 1 to 13, respectively. Chemicals 15 to 23 are identified as follows:
15. 2-phenylthiophene
16. 2,5-diphenylthiophene
17. 2-(p-isopropylphenyl)thiophene
18. 2-(m-chlorophenyl)thiophene
19. 2-(p-methoxyphenyl)thiophene
20. 2-(p-nitrophenyl)thiophene
21. 2,4-diphenylthiophene
22. 2-bromo-3,5-diphenylthiophene
23. 2,3,5-triphenylthiophene.

In a similar test the known chemical 2,5-bis(phenylthio)-thiophene (T. Fujisawa et al., cited above), which is outside the general formula given above, displayed miticidal activity, but was phytotoxic as evidenced by puckering of new growth. The known chemical 3,4-diphenylthiophene (H. J. Backer and W. Stevens, Rec. trav. chim., 59, 423 [1940]), which is outside the general formula given above, showed no miticidal activity. The known miticide 2-(p-t-butylphenoxy)cyclohexyl-2-propynyl sulfite was used at 80 ppm and 16 ppm for mite control comparisons in a similar test; the LD 95 for this chemical ranges from 20 to 100 ppm depending on environmental factors such as light intensity, temperature and humidity.

Table I

| Chemical | Mite Contact Test % Control |
|---|---|
| 1 | 100 |
| 2 | 75 |
| 3 | 97 |
| 4 | 85 |
| 5 | 100 |
| 6 | 98 |
| 7 | 100 |
| 8 | 100 |
| 9 | 98 |
| 10 | 100 |
| 11 | 100 |
| 12 | 50 |
| 13 | 60 |
| 14 | 98 |
| 15 | 45 |
| 16 | 100 |
| 17 | 100 |
| 18 | 40 |
| 19 | 100 |
| 20 | 100 |
| 21 | 100 |
| 22 | 100 |
| 23 | 100 |

EXAMPLE 16

Mite One-Day Residual Test

Cotton, *Gossypium hirsutum* L., variety Stoneville-213, in the second primary leaf stage, grown in twelve ounce cups under greenhouse conditions at 70°–75° F., was used in this test.

One plant (two primary leaves) in one pot was used for each replicate; two replicates were used for each concentration of the chemical tested.

Test compounds were prepared by dissolving 50 mg of chemical in one ml of acetone, adding one drop of Emulfor 719, a commercial surface-active dispersing agent (trademark; polyoxyethylated vegetable oil) and suspended in 50 ml of water for a concentration of 1000 ppm (parts per million). Aliquots were further diluted with distilled water to the concentration tested.

The plants were sprayed with the dispersions of the chemicals, using a small spray atomizer to thoroughly drench the foliage.

One day following treatment, a circle of tree tanglefoot was placed on the upper surfaces of the treated leaves, and adult mites were transferred into this confinement. Counts of these mites were made immediately following transfer and again six days later.

Abbott's formula was used to compensate for check mortality. The adjusted percent control was obtained by the following expression, wherein A is the adjusted % control, C is the % live mites on check plants and T is the % live mites on treated plants:

$$A = \frac{C - T}{C} \times 100$$

Data from the mite one-day residual test are shown in Table II, wherein the test chemicals have the numbers previously assigned.

Table II

| | Mite One Day Residual Test | | |
|---|---|---|---|
| | % Control | | |
| Chemical | 1000 PPM | 500 PPM | 100 PPM |
| 3 | 100 | 100 | — |
| 3 | — | 75 | 11 |
| 16 | 100 | 100 | 100 |
| 5 | 100 | 100 | 84 |
| 8 | 100 | 100 | 80 |
| 20 | 100 | 100 | 85 |
| 21 | 100 | 100 | 62 |
| 21 | — | 100 | 99 |
| 11 | 100 | 100 | 74 |
| 23 | 100 | 100 | 100 |
| 22 | 100 | 100 | 33 |

The following preparations illustrate additional compounds.

COMPOUND 24.

2,3-Diphenyl-5-p-tolylthiophene

In a 1-liter stainless steel autoclave equipped with stirrer were placed 71 g (0.217 mole) of 1,2-diphenyl-4-p-tolylbutane-1,4-dione, 100 ml of xylene, and 45 g (0.101 mole) of phosphorus pentasulfide. The autoclave was sealed, chilled in a Dry Ice-acetone bath, and charged with 120 g (3.52 moles) of hydrogen sulfide. The autoclave was then heated at 160°–190° C. (920–1130 psig) for 225 minutes. The autoclave was cooled to room temperature and the hydrogen sulfide vented into an aqueous sodium hydroxide solution. The residue in the autoclave was stirred with 150 ml of absolute ethanol. The slurry thus formed was filtered. The residue was dried to give 35.4 g (50.0%) of crude 2,3-diphenyl-5-p-tolylthiophene, m.p. 110°–112° C. Recrystallization from 190 ml. of toluene and 625 ml. of ethanol gave 30.1 g (42.5%) of pure 2,3-diphenyl-5-p-tolylthiophene, m.p. 114°–116° C.

Anal. Calcd. for $C_{23}H_{18}S$: C, 84.62; H, 5.56; S, 9.82. Found: C, 84.56; H, 5.69; S, 9.79.

COMPOUND 25.

2,3-Diphenyl-5-p-chlorophenylthiophene

In a 1-liter stainless steel autoclave equipped with stirrer were placed 76.9 g (0.220 mole) of 1,2-diphenyl-4-p-chlorophenylbutane-1,4-dione, 100 ml of xylene and 45 g (0.101 mole) of phosphorus pentasulfide. The autoclave was cooled with a Dry Ice-acetone bath and charged with 120 g (3.52 moles) of hydrogen sulfide. The autoclave was heated with stirring for 200 minutes at 155°–178° C. (1000–2000 psig). The autoclave was cooled and the hydrogen sulfide allowed to escape into a sodium hydroxide solution. The residue was stirred with 150 ml of absolute ethanol. Filtration and drying gave a crude product of 61.2 g (80.2%) m.p. 115°–117°. Recrystallization from 190 ml of toluene and 625 ml of ethanol gave 47.2 g (61.9%) of pure 2,3-diphenyl-5-p-chlorophenylthiophene, m.p. 121°–122° C.

Anal. Calcd. for $C_{22}H_{15}ClS$, C, 76.18; H, 4.36; Cl, 10.22. Found: C, 75.96; H, 4.38; Cl, 10.29

COMPOUND 26.

2,3-Di-p-anisyl-5-p-tolylthiophene

In a 1-liter stainless steel autoclave equipped with stirrer were placed 40.6 g (0.105 mole) of 1,2-di-p-anisyl-4-p-tolylbutene-1,4-dione, 100 ml of xylene and 25 g (0.056 mole) of phosphorus pentasulfide. The vessel was chilled with a Dry Ice-acetone bath and charged with 130 g (3.81 moles) of hydrogen sulfide. The autoclave was then heated with stirring for 215 minutes at 158°–165° C. (1250–1360 psig). After cooling the vessel, the hydrogen sulfide was allowed to vent into a sodium hydroxide solution. The residue was treated with 150 ml of absolute ethanol to destroy unreacted phosphorus pentasulfide. After removal of the ethanol there remained 70.5 g of crude product. Recrystallization from ethanol-dioxane (70:30) gave 20 g (49.3%) of pure 2,3-di-p-anisyl-5-p-tolythiophene, m.p. 99°–102° C. and a second crop of 6.5 g (16.0%) m.p. 92°–96° C.

Anal. Calcd. for $C_{25}H_{22}O_2S$: C, 77.69; H, 5.74; S, 8.30. Found: C, 77.15; H, 6.00; S, 8.16.

COMPOUND 27.

2,3-Di-p-anisyl-5-p-chlorophenylthiophene

In a 1-liter stainless steel autoclave equipped with stirrer were placed 54.5 g (0.133 mole) of 1,2-di-p-anisyl-4-p-chlorophenylbutane-1,4-dione, 100 ml of xylene and 30 g (0.0675 mole) of phosphorus pentasulfide. The autoclave was cooled with a Dry Ice-acetone bath and 130 g (3.81 moles) of hydrogen sulfide was distilled into the autoclave. The vessel was stirred and heated for three hours at 162°–168° C. (1220–1290 psig). After cooling to room temperature the hydrogen sulfide was vented into an aqueous sodium hydroxide solution. Treatment with 150 ml of absolute ethanol to remove unreacted phosphorus pentasulfide gave 77 g of crude product. Recrystallization from 400 ml of absolute ethanol gave 45 g (83.1%) of pure 2,3-di-p-anisyl-5-p-chlorophenylthiophene, m.p. 125°–128° C.

Anal. Calcd. for $C_{24}H_{19}ClO_2S$: C, 70.84; H, 4.71. Found: C, 69.81; H, 4.91.

COMPOUND 28.

2,3-Diphenyl-5-m-anisylthiophene

In a 1-liter stainless steel autoclave equipped with stirrer were placed 51.6 g (0.150 mole) of 1,2-diphenyl-4-m-anisylbutane-1,4-dione, 100 ml of xylene and 30 g (0.0675 mole) of phosphorus pentasulfide. The autoclave was cooled in Dry Ice and charged with 130 g (3.81 moles) of hydrogen sulfide. The mixture was then heated and stirred 235 minutes at 154°–177° C. (1120–1320 psig). The vessel was cooled to room temperature. The hydrogen sulfide was vented into a sodium hydroxide solution. The residue was treated with 150 ml of absolute ethanol to destroy excess phosphorus sulfides. Washing the product with another 330 ml of ethanol gave 32 g (62.3%) of crude product. Recrystallization from 50 ml of toluene and 150 ml of ethanol gave 19.8 g (38.5%) of pure 2,3-diphenyl-5-m-anisylthiophene, m.p. 100°–102° C.

Anal. Calcd. for $C_{23}H_{18}OS$: C, 80.66; H, 5.30; S, 9.36. Found: C, 80.41; H, 5.06; S, 9.35.

COMPOUND 29.

2,3-diphenyl-5-p-bromophenylthiophene

A mixture of 31.4 g (0.080 mole) of 1,2-diphenyl-4-p-bromophenylbutane-1,4-dione, 100 ml of xylene, 16 g (0.036 mole) of phosphorus pentasulfide and 125 g (3.67 mole) of hydrogen sulfide was heated in a 1-liter stainless steel autoclave with stirring for four hours at 156°–176° C. (1140–1320 psig). The reactor was cooled to room temperature and the hydrogen sulfide was led into a sodium hydroxide solution. Treatment of the residue with 150 ml of absolute ethanol gave 18.5 g (59.1%) of crude solid, m.p. 135°–137°. Recrystallization from 20 ml of dioxane and 60 ml. of absolute ethanol gave 16.5 g (52.7%) of pure 2,3-diphenyl-5-p-bromophenylthiophene.

Anal. Calcd. for $C_{22}H_{15}BrS$: C, 67.52; H, 3.86; Br, 20.42; S, 8.19. Found: C, 67.60; H, 3.86; Br, 20.70; S, 7.96.

COMPOUND 30.

2,3-Diphenyl-5-p-fluorophenylthiophene

A mixture 49.8 g (0.15 mole) of 1,2-diphenyl-4-p-fluorophenylbutane-1,4-dione, 100 ml of xylene, 30 g (0.0675 mole) of phosphorus pentasulfide and 130 g (3.81 moles) of hydrogen sulfide was heated and stirred in a 1-liter stainless steel autoclave for 4 hours at 157°–185° C. (620–1145 psig). After cooling the vessel to 20° C. and venting the hydrogen sulfide into a sodium hydroxide solution, the residue was stirred with 150 ml of absolute ethanol. Filtration gave 31.5 g (63.6%) of crude product, m.p. 108°–110° C. Recrystallization from 30 ml of dioxane and 90 ml of ethanol gave 24 g of pure 2,3-diphenyl-5-p-fluorophenylthiophene, m.p. 111°–113° C.

Anal. Calcd. for $C_{22}H_{15}FS$: C, 79.97; H, 4.58; S, 9.70. Found: C, 79.89; H, 4.46; S, 9.73.

COMPOUND 31.

2,3-Diphenyl-5-o-chlorophenylthiophene

A 1-liter stainless steel stirred autoclave was charged with 33 g. (0.0946 mole) of 1,2-diphenyl-4-o-chlorophenylbutane-1,4-dione, 100 ml. of xylene, 20 g of phosphorus pentasulfide and 125 g of hydrogen sulfide. The autoclave was then heated at 160°–187° C. for three hours. The autoclave was cooled and vented. The residue was washed with ethanol and filtered off to give 17 g (51.8%) of crude product, m.p. 103°–107° C. Recrystallization from 20 ml of dioxane and 40 ml of ethanol gave 10.5 g (32%) of pure product, m.p. 117°–118° C.

Anal. Calcd. for $C_{22}H_{15}ClS$: C, 76.18; H, 4.36; Cl, 10.22; S, 9.24. Found: C, 75.47; H, 4.24; C, 10.23; S, 9.27.

COMPOUND 32.

2,3-Diphenyl-5-(3,4-dichlorophenyl)thiophene

In a 1-liter stainless steel autoclave equipped with electrically-driven stirrer were placed 38.3 g. (0.100 mole) of 1,2-diphenyl-4-(3,4-dichlorophenyl)butane-1,4-dione, 100 ml of xylene, 20 g of phosphorus pentasulfide and 140 g of hydrogen sulfide. The reactor was heated for three hours at 160°–164° C. The crude product remaining after cooling and venting the reactor was stirred with ethanol. Filtration gave 30.5 g (80%) of solid m.p. 101°–103° C. Recrystallization from 30 ml of dioxane and 60 ml of ethanol gave 22.5 g (59%) of pure product, m.p. 106.2°–107.8° C.

Anal. Calcd. for $C_{22}H_{14}Cl_2S$: C, 69.30; H, 3.70; Cl, 18.59; S, 8.41. Found: C, 69.51; H, 3.71; Cl, 18.46; S, 8.18.

COMPOUND 33.

2,3-Diphenyl-5-p-methoxyphenylthiophene

In a 1-liter steel autoclave fitted with a mechanical stirrer, a thermometer and a pressure gauge were placed 32 g (0.09 mole) of 1,2-diphenyl-4-p-methoxyphenylbutane-1,4-dione, 100 ml of xylene, 20 g (0.045 mole) of phosphorus pentasulfide and 130 g of hydrogen sulfide. The mixture was stirred and heated 3 hours at 157°–162° C. (1190–1220 psig). The vessel was cooled and the hydrogen sulfide vented into an aqueous sodium hydroxide trap. The semisolid residue was stirred with 150 ml of absolute ethanol. Filtration gave 23 g (72%) of crude product, m.p. 130°–132° C. and a second crop of 3.7 g (11.6%) m.p. 124°–126° C. The two crops were combined and recrystallized from a mixture of 30 ml of dioxane and 60 ml of absolute ethanol to give 22 g (69%) of pure product m.p. 133°–134° C.

Anal. Calcd. for $C_{23}H_{18}OS$: C, 80.67; H, 5.30; S, 9.36. Found: C, 80.12; H, 5.31; S, 9.26.

COMPOUND 34.

2,3-Diphenyl-5-(3-fluoro-4-methoxyphenyl)thiophene

In a 1-liter autoclave were place 30 g (82.8 mmoles) of 1,2-diphenyl-4-(3-fluoro-4-methoxyphenyl)butane-1,4-dione, 100 ml of xylene, 18.4 g (41.4 mmoles) of phosphorus pentasulfide and 130 g of hydrogen sulfide. The vessel was heated 205 minutes at 155°–163' C. (1145–1235 psig.). The reactor was cooled and the hydrogen sulfide vented into a solution of 200 g of sodium hydroxide in 2 l of water. The semisolid residue was stirred with 150 ml of absolute ethanol. Filtration gave a first crop of 14.7 g (49.3%) m.p. 122°–125° C. Chilling the filtrate and refiltration gave a second crop of 10.5 g (35.2%), m.p. 118°–122° C. The two crops were combined and recrystallized from a mixture of 30 ml of dioxane and 70 ml of absolute ethanol to give 21.5 g (72.0%) of colorless plates, m.p. 123°–125° C.

Anal. Calc'd for $C_{23}H_{17}FOS$: C, 76.64; H, 4.75; S, 8.90. Found: C, 76.51; H, 4.68.

COMPOUND 35.

2,3-Diphenyl-5-p-t-butylphenylthiophene

A 1-liter stirred autoclave was charged with 55.6 g (0.150 mole) of 1,2-diphenyl-4-p-t-butylphenylbutane-1,4-dione, 100 ml of xylene, 33.3 g (0.075 mole) of phosphorus pentasulfide and 130 g of hydrogen sulfide. The reactor was cooled and vented. The residue was stirred with 150 ml of absolute ethanol. Filtration gave a first crop of 18 g (32.6%) m.p. 108°–112° C. Chilling the filtrate and refiltering gave a second crop of 24 g (43.4%) m.p. 102°–105° C. The two crops were combined for recrystallization from a mixture of 50 ml of dioxane and 100 ml of absolute ehtanol. The pure product (31.3 g, 56.6%) had a m.p. of 117°–119° C.

Anal. Calc'd for $C_{26}H_{24}S$: C, 84.74; H, 6.56; S, 8.70. Found: C, 85.26; H, 6.55; S, 8.39.

COMPOUND 36.

2,3-Bis(p-methoxyphenyl)-5-m-methylphenylthiophene p A 1-liter stainless steel autoclave equipped with mechanical stirrer was charged with 18.5 g of 1,2-bis(p-methoxyphenyl)-4-m-methylphenyl-1,4-butanedione, 100 ml of xylene, 10.6 g of phosphorus pentasulfide and 120 g of hydrogen sulfide. The mixtue was stirred and heated at 160°–165° C. for 2.9 hrs. The vessel was cooled, the hydrogen sulfide was vented and the residue stirred with 150 ml of ethanol to destroy unreacted phosphorus pentasulfide. Filtration and evaporation of solvent left 2,3-bis(p-methoxyphenyl)-5-m-methylphenylthiophene as a light yellow viscous oil.

COMPOUND 37.

2,3-Diphenyl-5-(3,4-dimethoxyphenyl)thiophene

In a 1-liter stainless steel autoclave fitted with mechanical stirrer were placed 37.4 g of 1,2-diphenyl-4-(3,4-dimethoxyphenyl)butane-1,4-diione, 100 ml of xylene, 22.2 g of phosphorus pentasulfide and 120 g of hydrogen sulfide. The mixture was stirred and heated at 162° for 3.25 hrs. The reactor was cooled to 10° C. The hydrogen sulfide was vented and the residue was stirred with 150 ml of ethanol; filtration and evaporation gave a residue of 2,3-diphenyl-5-(3,4-dimethoxyphenyl)thiophene as a viscous tan oil.

COMPOUND 38.

2,3-Diphenyl-5-(3,4,5-trimethoxyphenyl) thiophene

In a 1-liter stirred stainless steel autoclave were placed 40.4 g 1,2-diphenyl-4-(3,4,5-trimethoxyphenyl)-butane-1,4-dione, 100 ml of xylene, 22.2 g of phosphorus pentasulfide and 128 g of hydrogen sulfide. The reaction mixture was heated with stirring for 3 hours at 160°–168° C. (1210–1250 psig. pressure). The reactor was cooled to 10° C. and the hydrogen sulfide was released. The residue was stirred with 150 ml of ethanol to decompose unreacted phosphorus pentasulfide. Filtration and evaporation gave 38.8 g (96.4%) of 2,3-diphenyl-5-(3,4,5-trimethoxyphenyl)thiophene.

COMPOUND 39.

2,3-Diphenyl-5-(2,4-dimethoxyphenyl)thiophene

In a 1-l stainless steel autoclave were placed 56.2 g (0.150 mole) of 1,2-diphenyl-4-(2,4-dimethoxyphenyl)-butane-1,4-dione, 100 ml of xylene, 33.3 g (0.075 mole) of phosphorus pentasulfide and 120 g of hydrogen sulfide. The contents of the autoclave were stirred at 160°–162° C. (1040–1080 psig) for three hours. The autoclave was then cooled, and the remaining hydrogen sulfide was vented into a trap of aqueous sodium hydroxide. The residue was stirred with 150 ml of absolute ethanol to destroy excess phosphorus pentasulfide. Chilling to −78° C. and filtration gave 27.6 g (49.4%) of crude product, m.p. 107°–110° C. Recrystallization from 30 ml of dioxane and 60 mll of ethanol gave 17.3 g (31%) of pure 2,3-diphenyl-5-(2,4-dimethoxyphenyl)-thiophene, m.p. 112°–114° C.

Anal. Calc'd for $C_{24}H_{20}O_2S$: C, 77.39; H, 5.41; S, 8.61. Found: C, 77.01; H, 5.59; S, 9.46.

COMPOUND 40.

2,3-Diphenyl-5-(p-cyclopentylphenyl)thiophene

A 1-liter stainless steel stirred autclave was charged with 55 g (0.144 mole) of 1,2-diphenyl-4-p-cyclopentyl-phenylbutane-1,4-dione, 100 ml of xylene, 33 g (0.074 mole) of phosphorus pentasulfide and 100 g of hydrogen sulfide. The autoclave and contents were heated with stirring at 160°–170° C. (960–1030 psig) for three hours. The vessel was cooled and vented to release hydrogen sulfide into a trap of sodium hydroxide solution. The residue was stirred with 150 ml of ethanol to decompose excess phosphorus pentasulfide. Chilling to −78° C. gave 47.5 g (86.8%) of nearly pure product m.p. 149°–150° C. Recrystallization from 75 ml dioxane and 150 ml ethanol gave pure 2,3-diphenyl-5-(p-cyclopentylphenyl)thiophene, m.p. 149.5°–150.5° C.

Anal. Calc'd for $C_{27}H_{24}S$: C, 85.22; H, 6.36; S, 8.43. Found: C, 85.40; H, 6.14; S, 8.00.

COMPOUND 41.

2-m-Fluorophenyl-3,5-diphenylthiophene

In a 2-l three-necked flask fitted with reflux condenser, dropping funnel and mechanical stirrer were placed 6.1 g (0.25 g-atom) of magnesium and 200 ml of diethyl ether. From the dropping funnel was added a solution of 36.2 g (0.25 mole) of m-fluorobenzyl chloride in 100 ml of ether while the contents of the flask were stirred vigorously. The addition was completed in one hour. The mixture was stirred another thirty minutes and then treated with a solution of 50 g (0.238 mole) of 3-phenylpropiophenone in 250 ml of diethyl ether and 100 ml of tetrahydrofuran. The addition required one hour. The mixture was heated at reflux on a steam bath for another hour; then it was cooled and poured onto 1 kg of ice and 40 ml of concentrated hydrochloric acid. The hydrolysis mixture was extracted with one 300-ml and two 100-ml portions of chloroform. The extracts were combined, washed with 200 ml of water and evaporated down to give 78 g of crude 1-m-fluorophenyl-2,4-diphenylbutanol-2 which was heated for four hours at reflux with 20 ml of concentrated sulfuric acid and 80 ml of water. The organic phase was separated and washed with two 200 ml portions of distilled water. The second wash was neutral. The organic phase was dried in a rotary evaporator to give 77 g of crude 1-m-fluorophenyl-2,4-diphenylbutene-1. A 15-g (0.05-mole) aliquot of this triarylbutene was mixed with 4.8 g (0.15 g-atom) of sulfur and 3 drops of 1,5-diazabicyclo[4.3.0]non-5-ene and heated at 220°–230° C. for 22 hours. The reaction mixture was transferred to a sublimation apparatus and heated at 100° C. (0.02 mm Hg) to give 2.9 g of yellow needles. Recrystallization from dioxane-ethanol gave pure 2-m-fluorophenyl-3,5-diphenylthiophene as almost colorless needles, m.p. 118°–119° C.

Anal. Calc'd for $C_{22}H_{15}FS$: C, 79.97; H, 4.58. Found: C, 80.18; H, 4.31.

The infrared spectrum of the recrystallized product showed peaks at 695 and 746 cm$^{-1}$ (monosubstituted benzene ring) and at 790 and 845 cm$^{-1}$ (m-disubstituted benzene ring).

EXAMPLE 17

This example illustrates a citrus rust mite test. Grapefruit trees, of the variety Thompson Pink, were treated in this test conducted at Sanford, Florida. The trees were naturally infested with a population of the citrus rust mite, Phyllocoptruta oleivora, which is a pest that feeds on both foliage and fruit of citrus trees. Four replicate trees were treated with each chemical rate. Sprays were applied at 100 lbs. pressure with a spray gun which was used to drench the foliage. In the counting procedure, twenty-five leaves were sampled on each tree, 100 leaves per treatment. A one-square-inch area of each leaf was examined with a hand lens. A density index number was recorded for each leaf examined as follows: 0=no mites, 1=1–2 mites, 2=3–6 mites, 3=7 or more mites. These index numbers were then totalled and divided by the number of leaves to provide an average density rating.

The percent reduction of citrus rust mite density over the untreated checks was then calculated by adaptatin of Abbott's formula.

$$\% \text{ Reduction} = \frac{\text{Density Rating Check - Treated}}{\text{Density rating of check}} \times 100$$

Counts were made at intervals after treatment, as indicated in the tables III, IV and V.

The results on Table III indicate that the compounds of this invention compare most favorably with a widely used commercial product where the long range control of citrus rust mites is concerned. Tables IV and V provide evidence that additional compounds of this invention are most suitable for the control of citrus rust mites.

TABLE III

Percent Reduction of Citrus Rust Mite Density Over the Untreated Check

| Compound | #AI/A* | PPM | Days Post-Treatment ||||| 
|---|---|---|---|---|---|---|---|
| | | | 11 | 27 | 47 | 60 | 90 |
| 23 | 0.22 | 50 | 88.3 | 87.4 | 85.4 | 78.9 | 47.7 |
| 23 | 0.44 | 100 | 97.4 | 98.2 | 97.4 | 90.3 | 50.3 |
| 23 | 0.88 | 200 | 94.8 | 87.4 | 94.0 | 90.3 | 54.0 |
| 23 | 1.76 | 400 | 97.4 | 94.6 | 94.7 | 94.2 | 91.1 |
| 21 | 0.44 | 100 | 75.3 | 13.5 | 8.6 | 0.0 | — |
| 21 | 0.88 | 200 | 96.1 | 80.1 | 28.5 | 23.0 | — |
| 21 | 1.96 | 400 | 97.4 | 65.7 | 48.3 | 42.3 | — |
| 21 | 3.92 | 800 | 100 | 81.9 | 70.9 | 48.0 | 32.4 |
| Prior Art** | 0.63 | 150 | 97.4 | 89.2 | 78.8 | 55.8 | 24.8 |
| Untreated Check | 0 | 0 | 0 | 0 | 0 | 0 | 0 |

*Active ingredient/lbs. per acre.
**Prior Art Chemical-Chlorobenzilate (ethyl-4,4'-dichlorobenzilate)

TABLE IV

Percent Reduction of Citrus Rust Mite Density Over the Untreated Check

| Compound | Rate PPM | Days Post-Treatment |||
|---|---|---|---|---|
| | | 13 | 35 | 50 |
| 24 | 100 | 96.7 | 79 | 75 |
| 25 | 100 | 100 | 70 | 32 |

TABLE V*

Percent Reduction of Citrus Rust Mite Density Over the Untreated Check

| Compound | Rate PPM | 10 Days Post-Treatment |
|---|---|---|
| 23 | 200 | 65 |
| 26 | 200 | 35 |
| 28 | 200 | 15 |
| 30 | 200 | 43 |
| 27 | 200 | 63 |

*10 leaves counted/rep. Each rep. equalled a 12-inch branch tip isolated with Tanglefoot.

EXAMPLE 18

A mite contact test is carried out according to the procedure of Example 15 (two-spotted spider mites on cotton), using the compounds shown in Table VI, at a concentration of 1000 and 500 ppm, with the results shown in said table.

TABLE VI

Mite Contact Test

| | % Control | |
|---|---|---|
| Compound | 1000 PPM | 500 PPM |
| 24 | 92 | 83 |
| 25 | 98 | 100 |
| 26 | 98 | 73 |
| 28 | 100 | 100 |
| 30 | 100 | 97 |
| 29 | 41 | 18 |
| 27 | 40 | 21 |
| 31 | 93 | 86 |
| 32 | 99 | 88 |
| 33 | 100 | 96 |
| 34 | 100 | 100 |
| 35 | 100 | 83 |
| 39 | 98 | 100 |

A preferred sub-class of substituted thiophenes of the invention are those of the formula previously stated wherein Y and Z are phenyl and A is phenyl having 1 to 3 substituents which may be the same or different and are selected from fluorine, chlorine, $C_1$-$C_4$ alkyl, especially methyl, isopropyl, tertiary butyl, and methoxy; provided at least one substituent is fluorine or chlorine. More preferred are such compounds wherein said substituents are selected from fluorine, chlorine and methoxy. Especially preferred are such compounds wherein said substituents are selected from fluorine and chlorine. Of particular interest are such compounds wherein A, Y and Z have one of the following sets of values:

| Compound No. | A | Y | Z |
|---|---|---|---|
| 25 | p-ClC$_6$H$_4$ | C$_6$H$_5$ | C$_6$H$_5$ |
| 31 | o-ClC$_6$H$_4$ | C$_6$H$_5$ | C$_6$H$_5$ |
| 32 | 3,4-Cl$_2$C$_6$H$_3$ | C$_6$H$_5$ | C$_6$H$_5$ |
| 30 | p-FC$_6$H$_4$ | C$_6$H$_5$ | C$_6$H$_5$ |
| 34 | 3-F,4-OCH$_3$C$_6$H$_3$ | C$_6$H$_5$ | C$_6$H$_5$ |

Compounds of the preferred sub-class have superior long-term miticidal activity compared to certain prior art compounds. This superiority is particularly evident in tests carried out for prolonged periods of 3 to 5 weeks. Such superior performance is maintained either in open sunlight or under light-shaded conditions.

Compounds of the preferred sub-class are remarkable for their superior efficacy in the control of citrus rust mites, a particularly difficult pest to control.

EXAMPLE 19

Field tests are conducted at Sanford, Florida for control of citrus rust mites on orange trees. The tests are performed on single whole trees, with three replications. In these tests, the number of citrus mites per square inch in each of six counts made at regular intervals is added. These sums are then compared to those of untreated check trees. By adaptation of Abbott's formula a percent control value for each treatment is obtained. The test compound is applied by spraying the trees, at a concentration of active compound shown in Table VII. Usually only those treatments that are giving superior control are continued for the full five weeks in these tests.

Table VII

% Control of Citrus Rust Mites on Oranges at Various ppm

Y and Z = phenyl*
Conc. of Test Compound, ppm:

| Comp. No. | A | 3 weeks | | 5 weeks | |
|---|---|---|---|---|---|
| | | 12.5 | 25 | 12.5 | 25 |
| 23 | C$_6$H$_5$ | 63 | 67 | 53 | 58 |
| 24 | p-CH$_3$C$_6$H$_4$ | 50 | 64 | — | — |
| 25 | p-ClC$_6$H$_4$ | 73 | 89 | 77 | 84 |
| 31 | o-ClC$_6$H$_4$ | 78 | 83 | 65 | 80 |
| 32 | 3,4-Cl$_2$C$_6$H$_3$ | 77 | 87 | 74 | 86 |
| 30 | p-FC$_6$H$_4$ | 69 | 89 | 58 | 89 |
| 34 | 3-F,4-OCH$_3$C$_6$H$_4$ | 64 | 82 | 60 | 73 |
| 35 | p-C(CH$_3$)$_3$C$_6$H$_4$ | 73 | 67 | — | — |
| 28 | m-OCH$_3$C$_6$H$_4$ | 42 | 52 | — | — |
| 33 | p-OCH$_3$C$_6$H$_4$ | 57 | 38 | — | — |
| 27* | p-ClC$_6$H$_4$ | 54 | 65 | — | — |

*except in Compound No. 27, wherein Y and Z are p-OCH$_3$C$_6$H$_4$

The data in Table VII show the remarkably prolonged superior effectiveness of new Compounds Nos. 25, 31, 32, 30 and 34 as compared to prior art Compounds Nos. 23 and 24.

EXAMPLE 20

The field test described in Example 19 was repeated but limiting the investigation to a selected number of compounds. The results are summarized in Table VIII.

Table VIII

% Control of Citrus Rust Mites on Oranges at Various ppm After 5 Weeks

Y and Z are phenyl
Concentration of Test Compound, ppm:

| Comp. No. | A | 25 | 50 |
|---|---|---|---|
| 23 | C$_6$H$_5$ | 48 | 80 |
| 25 | p-ClC$_6$H$_4$ | 95 | 98 |
| 31 | o-ClC$_6$H$_4$ | 45 | — |
| 32 | 3,4-Cl$_2$C$_6$H$_3$ | 90 | 96 |
| 30 | p-FC$_6$H$_4$ | 88 | — |
| 34 | 3-F,4-(CH$_3$O)C$_6$H$_3$ | 58 | — |

The data in Table VIII substantially confirm the results of the previous example, namely, that the new chemicals of the preferred sub-class are superior to the prior art compound. The efficacy of Compound No. 31 is essentially identical to the prior art Compound No. 23, yet, in the previous example the significant superiority of No. 31 over No. 23 has already been demonstrated.

We claim:

1. A method of controlling acarid pests comprising contacting the acarid pests with an acaricidal amount of a substituted thiophene of the formula

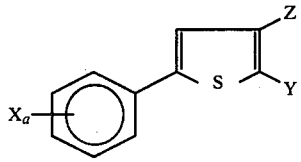

where X is alkyl having 1 to 3 carbon atoms, halogen, nitro, haloalkyl having 1 to 3 carbon atoms, alkoxy having 1 to 3 carbon atoms, alkylthio having 1 to 3 carbon atoms or phenyl; a is 0, 1 or 2; Y is hydrogen, halogen, phenyl, phenylthio, nitrophenylthio, chlorophenylthio, or phenylsulfono; and Z is hydrogen or phenyl.

2. A method as in claim 1 in which the said pests which are contacted with said substituted thiophene are mites located on plant life.

3. A method as in claim 1 in which the pests are mites and the substituted thiophene is 2-(p-methylthiophenyl)thiophene.

4. A method as in claim 1 in which the pests are mites and the substituted thiophene is 2-(o-biphenylyl)thiophene.

5. A method as in claim 1 in which the pests are mites and the substituted thiophene is 2-phenyl-5-(phenylthio)thiophene.

6. A method as in claim 1 in which the pests are mites and the substituted thiophene is 2-phenyl-5-(phenylsulfonyl)thiophene.

7. A method as in claim 1 in which the pests are mites and the substituted thiophene is 2-phenylthio-5-p-tolylthiophene.

8. A method as in claim 1 in which the pests are mites and the substituted thiophene is 2-(p-isopropylphenyl)-5-(phenylthio)thiophene.

9. A method as in claim 1 in which the pests are mites and the substituted thiophene is 2-(m-chlorophenyl)-5-(phenylthio)thiophene.

10. A method as in claim 1 in which the pests are mites and the substituted thiophene is 2-phenylthio-5-(m-trifluoromethylphenyl)thiophene.

11. A method as in claim 1 in which the pests are mites and the substituted thiophene is 2-(3,4-xylyl)thiophene.

12. A method as in claim 1 in which the pests are mites and the substituted thiophene is 2-phenylthio-5-(3,4-xylyl)thiophene.

13. A method as in claim 1 in which the pests are mites and the substituted thiophene is 3,5-diphenyl-2-(phenylthio)thiophene.

14. A method as in claim 1 in which the pests are mites and the substituted thiophene is 2-(p-bromophenyl)-5-(m-nitrophenylthio)thiophene.

15. A method as in claim 1 in which the pests are mites and the substituted thiophene is 2-p-anisyl-5-(phenylthio)thiophene.

16. A method as in claim 1 in which the pests are mites and the substituted thiophene is 2-(p-chlorophenylthio)-5-phenylthiophene.

17. A method as in claim 1 in which the pests are mites and the substituted thiophene is 2-phenylthiophene.

18. A method as in claim 1 in which the pests are mites and the substituted thiophene is 2,5-diphenylthiophene.

19. A method as in claim 1 in which the pests are mites and the substituted thiophene is 2-(p-isopropylphenyl)thiophene.

20. A method as in claim 1 in which the pests are mites and the substituted thiophene is 2-(m-chlorophenyl)thiophene.

21. A method as in claim 1 in which the pests are mites and the substituted thiophene is 2-(p-methoxyphenyl)thiophene.

22. A method as in claim 1 in which the pests are mites and the substituted thiophene is 2-(p-nitrophenyl)thiophene.

23. A method as in claim 1 in which the pests are mites and the substituted thiophene is 2,4-diphenylthiophene.

24. A method as in claim 1 in which the pests are mites and the substituted thiophene is 2-bromo-3,5-diphenylthiophene.

25. A method as in claim 1 in which the pests are mites and the substituted thiophene is 2,3,5-triphenylthiophene.

26. A method of controlling acarid pests comprising contacting the acarid pests with an acarididal amount of a substituted thiophene of the formula

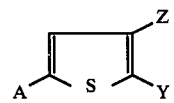

wherein A, Y and Z may be the same or different and are as follows:

A is phenyl, naphthyl, or substituted phenyl carrying one or more substituents, said substituents being fluorine, chlorine, bromine, nitro, alkyl having 1 to 5 carbon atoms, cycloalkyl having 5 or 6 carbon atoms, phenyl, alkoxy having 1 to 3 carbon atoms, alkylthio having 1 to 3 carbon atoms, alkylenedioxy having 1 or 2 carbon atoms or halomethyl having 1 to 3 halogen atoms selected from fluorine, chlorine and bromine;

Y has the meanings of A and additionally may be hydrogen, fluorine, chlorine, bromine, phenylthio, phenylsulfono or phenylthio substituted with one or more of the substituents fluorine, chlorine, bromine, nitro, alkyl having 1 to 5 carbon atoms, cycloalkyl having 5 or 6 carbon atoms, alkoxy having 1 to 3 carbon atoms or halomethyl having 1 to 3 halogen atoms selected from fluorine, chlorine and bromine; and Z is hydrogen, phenyl or phenyl having one or more substituents selected from fluorine, bromine, chlorine, nitro, alkyl having 1 to 5 carbon atoms, alkoxy having 1 to 3 carbon atoms and halomethyl having 1 to 3 halogen atoms selected from fluorine, chlorine and bromine.

27. The method of claim 26 wherein A is phenyl, phenyl substituted with fluorine, chlorine, alkyl having 1 to 4 carbon atoms, phenyl, methoxy, methylthio, trifluoromethyl or nitro; Y is hydrogen, bromine, phenyl, phenylthio or substituted phenyl or phenylthio having substituents selected from chlorine and methoxy; and Z is hydrogen, phenyl or phenyl substituted with fluorine, chlorine or methoxy.

28. The method of claim 26 wherein the said substituted thiophene is 5-p-t-butylphenyl-2,3-diphenylthiophene.

29. The method of claim 26 wherein the said substituted thiophene is 5-m-methoxyphenyl-2,3-diphenylthiophene.

30. The method of claim 26 wherein the said substituted thiophene is 5-o-methoxyphenyl-2,3-diphenylthiophene.

31. The method of claim 26 wherein the said substituted thiophene is 5-p-methoxyphenyl-2,3-diphenylthiophene.

32. The method of claim 26 wherein wherein the said substituted thiophene is 5-p-fluorophenyl-2,3-diphenylthiophene.

33. The method of claim 26 wherein the said substituted thiophene is 5-(3-fluoro-4-methoxyphenyl)-2,3-diphenylthiophene.

34. The method of claim 26 wherein the said substituted thiophene is 5-o-chlorophenyl-2,3-diphenylthiophene.

35. The method of claim 26 wherein the said substituted thiophene is 5-p-chlorophenyl-2,3-diphenylthiophene.

36. The method of claim 26 wherein the said substituted thiophene is 2,3-bis(p-methoxyphenyl)-5-p-tolylthiophene.

37. The method of claim 26 wherein the said substituted thiophene is 5-(2,4-dimethoxyphenyl)-2,3-diphenylthiophene.

38. The method of claim 26 wherein the said substituted thiophene is 5-p-tolyl-2,3-diphenylthiophene.

39. A substituted thiophene of the formula

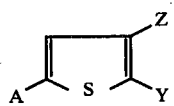

wherein Y and Z are phenyl and A is phenyl having 1 to 3 substituents which may be the same or different and are selected from fluorine, chlorine, alkyl having 1 to 4 carbon atoms, and methoxy; provided at least one substituent is fluorine or chlorine.

40. The compound of claim 39 wherein said substituents are selected from fluorine, chlorine and methoxy.

41. The method of claim 40 wherein said substituents are selected from fluorine and chlorine.

42. The compound of claim 39 wherein A, Y and Z have one of the following sets of values:

| A | Y | Z |
|---|---|---|
| p-ClC$_6$H$_4$ | C$_6$H$_5$ | C$_6$H$_5$ |
| o-ClC$_6$H$_4$ | C$_6$H$_5$ | C$_6$H$_5$ |
| 3,4-Cl$_2$C$_6$H$_3$ | C$_6$H$_5$ | C$_6$H$_5$ |
| p-FC$_6$H$_4$ | C$_6$H$_5$ | C$_6$H$_5$ |
| 3-F,4-OCH$_3$C$_6$H$_3$ | C$_6$H$_5$ | C$_6$H$_5$ |

43. The substituted thiophene of claim 39 which is 5-p-fluorophenyl-2,3-diphenylthiophene.

44. The substituted thiophene of claim 39 which is 5-(3-fluoro-4-methoxyphenyl)-2,3-diphenylthiophene.

45. The substituted thiophene of claim 39 which is 5-o-chlorophenyl-2,3-diphenylthiophene.

46. The substituted thiophene of claim 39 which is 5-p-chlorophenyl-2,3-diphenylthiophene.

47. A miticidal composition comprising a compound as in claim 39 in miticidally effective amount, in admixture with a carrier therefor.

48. A miticidal composition comprising a compound as in claim 40 in miticidally effective amount, in admixture with a carrier therefor.

49. A miticidal composition comprising a compound as in claim 41 in miticidally effective amount, in admixture with a carrier therefor.

50. A citrus rust miticidal composition comprising a compound as in claim 42 in citrus rust miticidal amounts, in admixture with a surface active agent.

51. The composition of claim 50 in which said compound is 2,3-diphenyl-5-p-chlorophenylthiophene.

52. A method of controlling citrus rust mite pests comprising contacting said pests or the habitat of said pests with a citrus rust miticidally effective amount of a substituted thiophene as in claim 39.

53. A method of controlling citrus rust mite pests comprising contacting said pests or the habitat of said pests with a citrus rust miticidally effective amount of a substituted thiophene as in claim 40.

54. A method of controlling citrus rust mite pests comprising contacting said pests or the habitat of said pests with a citrus rust miticidally effective amount of a substituted thiophene as in claim 41.

55. A method of controlling citrus rust mite pests comprising contacting said pests or the habitat of said pests with a citrus rust miticidally effective amount of a substituted thiophene as in claim 42.

56. A method as in claim 55 in which the substituted thiophene is 2,3-diphenyl-5-p-chlorophenylthiophene.

* * * * *